US011177040B2

(12) United States Patent
Gupta et al.

(10) Patent No.: US 11,177,040 B2
(45) Date of Patent: Nov. 16, 2021

(54) RISK IDENTIFICATION AND RESPONSE (71) Applicant: Health Solutions Research, Inc., Rockville, MD (US)

(72) Inventors: Ajay Kumar Gupta, Potomac, MD (US); Ramani Peruvemba, McLean, VA (US)

(73) Assignee: HEALTH SOLUTIONS RESEARCH, INC., Rockville, MD (US)

( * ) Notice: Subject to any disclaimer, the term of this patent is extended or adjusted under 35 U.S.C. 154(b) by 353 days.

(21) Appl. No.: 16/024,387

(22) Filed: Jun. 29, 2018

(65) Prior Publication Data
US 2018/0374580 A1 Dec. 27, 2018

Related U.S. Application Data (60) Provisional application No. 62/602,661, filed on May 1, 2017.

(51) Int. Cl.
*G16H 50/30* (2018.01)
*G16H 10/60* (2018.01)
(Continued)

(52) U.S. Cl.
CPC ........... *G16H 50/30* (2018.01); *G16H 10/60* (2018.01); *G16H 50/80* (2018.01); *G16H 70/40* (2018.01)

(58) Field of Classification Search
CPC .... G06F 1/00–2221/2153; G16H 10/00–80/00
See application file for complete search history.

(56) References Cited

U.S. PATENT DOCUMENTS

| 8,758,238 | B2 * | 6/2014 | Clapp | G06F 19/3418 |
| | | | | 600/300 |
| 2005/0131740 | A1 * | 6/2005 | Massenzio | G06Q 50/22 |
| | | | | 705/2 |

(Continued)

FOREIGN PATENT DOCUMENTS

WO   WO-2016172614 A1 * 10/2016 ............. G16H 50/20

OTHER PUBLICATIONS

Chen et al., "Reality mining: A prediction algorithm for disease dynamics based on mobile big data," Information Sciences 379 (2017) 82-93 (Year: 2017).*

*Primary Examiner* — Elaine Gort
*Assistant Examiner* — Jonathon A. Szumny
(74) *Attorney, Agent, or Firm* — Hamre, Schumann, Mueller & Larson, P.C.

(57) ABSTRACT

A method, system, and computer-readable medium to stratify a health risk acquires structured information and unstructured information from a plurality of sources, converts at least some of the unstructured information to structured information, and geocodes the acquired structured information and converted structured information to produce geocoded data. Health information of a plurality of subjects are similarly geocoded to produce geocoded subject health data and merged with the geocoded data and mapped to a dashboard. First geographical correlations between at least some of the health information and the structured and unstructured information derived from the merged geocoded data and geocoded subject health data are output for display, and a risk stratification base score is developed in accordance with second geographical correlations between at least some of the health information and the acquired structured and unstructured information derived from the merged geocoded data and geocoded subject health data. The risk stratification base score is adjusted in accordance (Continued)

with positive and/or negative variables, and a total risk score is determined from the adjusted risk stratification base score and output for integration into an electronic health records system.

19 Claims, 6 Drawing Sheets

(51) Int. Cl.
*G16H 50/80* (2018.01)
*G16H 70/40* (2018.01)

(56) References Cited

U.S. PATENT DOCUMENTS

| | | | | |
|---|---|---|---|---|
| 2006/0129427 A1* | 6/2006 | Wennberg | G06Q 40/08 | 705/2 |
| 2008/0091471 A1* | 4/2008 | Michon | G16H 50/70 | 705/3 |
| 2011/0288886 A1* | 11/2011 | Whiddon | G16H 70/40 | 705/3 |
| 2013/0197942 A1* | 8/2013 | Chiu | G16H 50/30 | 705/3 |
| 2014/0081652 A1* | 3/2014 | Klindworth | G06Q 20/4016 | 705/2 |
| 2014/0236668 A1* | 8/2014 | Young | G16H 10/20 | 705/7.28 |
| 2015/0242586 A1* | 8/2015 | Kagen | G06F 19/324 | 705/2 |
| 2016/0110512 A1* | 4/2016 | Adjaoute | G06F 19/328 | 705/2 |
| 2016/0314256 A1* | 10/2016 | Su | G16H 50/50 | |
| 2016/0378932 A1* | 12/2016 | Sperling | G06Q 40/08 | 705/3 |
| 2017/0004275 A1* | 1/2017 | Mehta | G06N 7/005 | |
| 2017/0061077 A1* | 3/2017 | Cline | G06F 19/00 | |
| 2017/0076058 A1* | 3/2017 | Stong | G16H 70/40 | |
| 2017/0103172 A1* | 4/2017 | Fink | G06N 3/0454 | |
| 2017/0109493 A1* | 4/2017 | Hogg | G06F 19/3456 | |
| 2017/0132371 A1* | 5/2017 | Amarasingham | G06F 16/9535 | |
| 2017/0286622 A1* | 10/2017 | Cox | G16H 50/30 | |
| 2017/0351834 A1* | 12/2017 | Cahan | G16H 70/60 | |
| 2019/0088356 A1* | 3/2019 | Oliver | G16H 40/20 | |

* cited by examiner

RISK IDENTIFICATION AND RESPONSE

TECHNICAL FIELD

The present disclosure relates to risk stratification and, in one or more embodiments, to developing a risk stratification (levels of risk) from disparate sources of data (e.g., demographic, geographic, and social data) to identify subjects who may be at risk for addiction to, diverting, or overdose of a drug, of which opioids and fentanyl are but two examples.

BACKGROUND

Many examples of risk analysis call for identifying risks and populations subject to such risks, and correlating the risks to the subject population in accordance with various factors. One such example is the identification of people at risk for drug dependence or addiction, of which opioid addiction is a rapidly growing problem.

Opioid addiction has many contributing root causes. Unfortunately, no approach exists that considers comprehensively the many factors that may contribute to opioid addiction, such as the different types of opioids or narcotics (including legally prescribed opioids, illegally diverted prescribed opioids, and illegal opioids such as heroin or illegally manufactured fentanyl), or the numerous sources of opioids, both licit and illicit (including physician's offices, pharmacies, hospitals, behavioral health clinics, or the variety of illegal sources). Further, no approach exists that readily, comprehensively, and effectively assesses an individual's sensitivity to opioids based on such factors and other data from disparate sources, and that customizes action on behalf of the individual accordingly.

SUMMARY

In a first aspect, a method to stratify a health risk comprises: acquiring structured information and unstructured information from a plurality of sources; converting at least some of the unstructured information to structured information; geocoding the acquired structured information and converted structured information to produce geocoded data; geocoding health information of a plurality of subjects to produce geocoded subject health data; merging the geocoded data and geocoded subject health data; mapping the merged geocoded data and geocoded subject health data to a dashboard; via the dashboard, outputting for display a map visualizing first geographical correlations between at least some of the health information and the acquired structured and unstructured information derived from the merged geocoded data and geocoded subject health data; developing a risk stratification base score in accordance with second geographical correlations between at least some of the health information and the acquired structured and unstructured information derived from the merged geocoded data and geocoded subject health data; adjusting the risk stratification base score in accordance with positive and/or negative variables; determining a risk score from the adjusted risk stratification base score; and outputting the risk score formatted for integration into an electronic health records system.

In a second aspect, a system to stratify risk comprises: a memory to store structured information and unstructured information; and a processor configured to: convert at least some of the unstructured information to structured information; geocode the stored structured information and converted structured information to produce geocoded data; store the geocoded data in a database in the memory; geocode health information of a plurality of subjects to produce geocoded subject health data; store the geocoded subject health data in the database; merge the geocoded data and geocoded subject health data; map the merged geocoded data and geocoded subject health data to a dashboard; in response to a request via the dashboard, output for display a map visualizing first geographical correlations between at least some of the health information and the structured and unstructured information derived from the merged geocoded data and geocoded subject health data; develop a risk stratification base score in accordance with second geographical correlations between at least some of the health information and the structured and unstructured information derived from the merged geocoded data and geocoded subject health data; adjust the risk stratification base score in accordance with positive and/or negative factors; determine a risk score from the adjusted risk stratification base score; and output the risk score formatted for integration into an electronic health records system.

In a third aspect, a non-transitory computer-readable medium has computer-readable instructions that, if executed by a computing device, cause the computing device to perform operations comprising: geocoding demographic, geographic, and social data; geocoding health information of a plurality of subjects to produce geocoded subject health data; merging the geocoded demographic, geographic, and social data and geocoded subject health data; mapping the merged geocoded demographic, geographic, and social data and geocoded subject health data to a dashboard; via the dashboard, outputting for display a map visualizing first geographical correlations between at least some of the demographic, geographic, and social data and health information derived from the merged geocoded demographic, geographic, and social data and geocoded subject health data; developing a risk stratification base score in accordance with second geographical correlations between at least some of the demographic, geographic, and social data and health information derived from the merged geocoded demographic, geographic, and social data and geocoded subject health data; adjusting the risk stratification base score in accordance with positive and/or negative variables; determining a risk score from the adjusted risk stratification base score; and outputting the risk score formatted for integration into an electronic health records system.

BRIEF DESCRIPTION OF THE DRAWINGS

In the detailed description that follows, embodiments are described as illustrations only since various changes and modifications will become apparent to those skilled in the art from the following detailed description. The use of the same reference numbers in different figures indicates similar or identical items.

DETAILED DESCRIPTION

In the following detailed description, reference is made to the accompanying drawings, which form a part of the description. In the drawings, similar symbols typically identify similar components, unless context dictates otherwise. Furthermore, unless otherwise noted, the description of each successive drawing may reference features from one or more of the previous drawings to provide clearer context and a more substantive explanation of the current example embodiment. Still, the example embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein and illustrated in the drawings, may be arranged, substituted, combined, separated, and designed in a wide variety of different configurations, all of which are explicitly contemplated herein.

One or more embodiments disclosed herein are presented in the context of risk stratification for individuals at risk of opioid addiction. The Opioid Abuse Related Mortality (OARM) is a risk stratification mechanism that allows for the early identification of patients or other subjects at imminent risk for opioid-related trouble. The mechanism may be developed by analysis of electronic health records utilizing natural language processing (NLP) on multiple data sets, both structured and unstructured. The result is the OARM, an artificial intelligence solution, that allows for the early identification and treatment of high risk individuals and populations. Such embodiments are illustrative and not intended to be limited by the context.

Figure 1A:
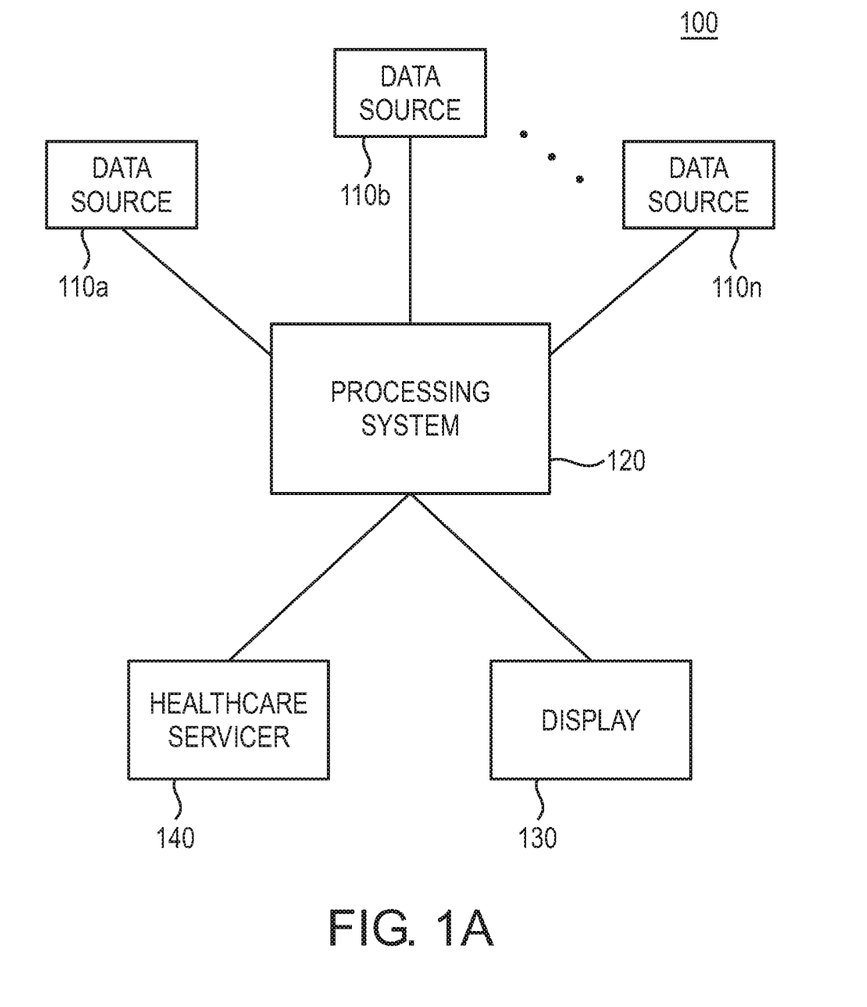
FIG. 1A shows an example configuration of a system in which risk stratification may be implemented, arranged in accordance with at least some embodiments described herein.

FIG. 1 shows an example configuration of a system 100 in which risk stratification may be implemented, arranged in accordance with at least some embodiments described herein. FIG. 1 shows a plurality of health and non-health data sources 110a, 110b, . . . 110n (collectively, "data sources 110" hereafter), which may be communicatively coupled to a processing system 120. Processing system 120 may be communicatively coupled to a display 130 and a health care servicer 140. By way of example and without limitation, one or more of the communicative couplings may be wired or wireless connections as would be understood by one of ordinary skill in the art.

Data sources 110 may provide, for example, information relating to one or more of geographic, demographic, transportation, economic, health system, law enforcement, social (including social media), socioeconomic, and historical health data, which may be analyzed for correlations with one another and with a subject population and/or individual subjects in the population. In the context of drug abuse risks, examples of such information may include, but are not limited to, drug sources, drug-related incidents (e.g., drug-related crimes, overdoses, violence), structured and unstructured health data (e.g., clinician's notes or discharge summaries) from EHR (electronic health record) systems, social determinants (for example, economic, income, education, etc.) of health data, overdose rates, and clinician behavior (e.g., opioid prescription habits including total opioid prescriptions written, and ordering additional monitoring or behavioral health consultation, etc.).

Figure 1B:
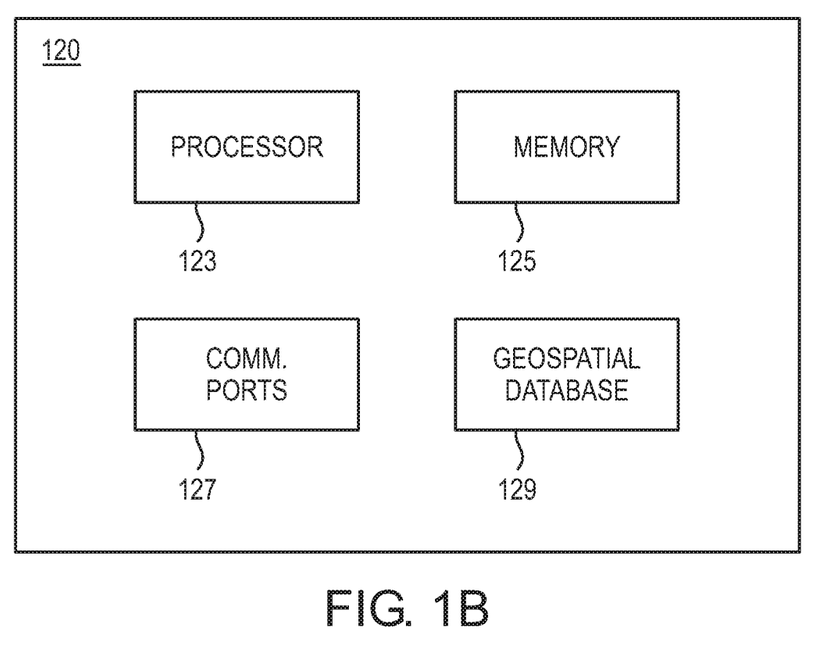
FIG. 1B shows an example configuration of a processing system that may be implemented, arranged in accordance with at least some embodiments described herein.

FIG. 1B shows an example configuration of a processing system that may be implemented, arranged in accordance with at least some embodiments described herein. In one or more embodiments, processing system 120 may include one or more processors or computing devices 123 (collectively, "processor" as used herein), a system memory 125, communication ports 127 to acquire data from one or more of data sources 110, and a geospatial database 129. Processing system 120 may be configured and arranged to implement a geographic information system platform with a data analytic engine as discussed below. Acquired data may be geocoded according to a process described below and added to geospatial database 129. The stored geocoded data may be analyzed using geospatial data analytics, merged with subject data, and organized for mapping to geographic locations and formatted for output for any suitable purpose, including for display on a geographic or other map via display 130, or for further analysis or review (e.g., personal or machine) either locally or remotely (e.g., at a hospital or other healthcare setting 140).

Figure 2:
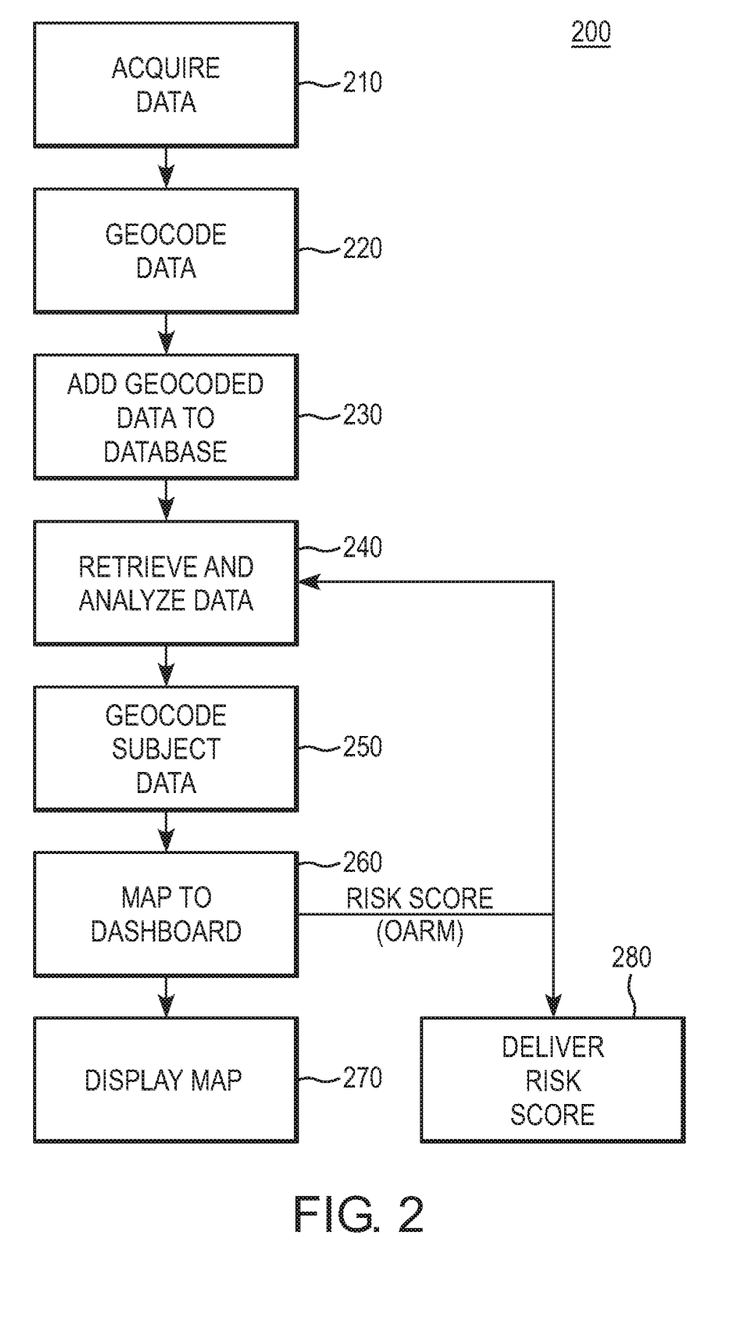
FIG. 2 shows an example processing flow 200 by which a subject risk stratification for Opioid Abuse Related Mortality (OARM) may be obtained, arranged in accordance with at least some embodiments described herein.

FIG. 2 shows an example processing flow 200 by which a subject risk stratification for Opioid Abuse Related Mortality (OARM) may be obtained, arranged in accordance with at least some embodiments described herein. Processing flow 200 may include one or more operations, actions, or functions depicted by one or more blocks 210, 220, 230, 240, 250, 260 and 270. Although illustrated as discrete blocks, various blocks may be divided into additional blocks, combined into fewer blocks, or eliminated, depending on the desired implementation. As a non-limiting example, the description of processing flow 200, corresponding to the depiction thereof in FIG. 2 and performed by processing system 120 in one or more embodiments described herein, pertains to obtaining a subject risk stratification of OARM. Processing may begin at block 210.

Block 210 (Acquire Data) may refer to processing system 120 receiving data from data sources 110 via communication ports 127. Data may be acquired in one or more of a variety of ways, including but not limited to wireless or wired communications from data sources 110 or manual entry (for example, by an operator using a keyboard or tablet, smartphone, etc. utilizing appropriate application software). Block 210 may be followed by Block 220.

Block 220 (Geocode Data) may refer to processor 123 associating acquired data with geographical locations for use in a geospatial healthcare dashboard. Additionally or alternatively, in one or more embodiments, acquired data may already have a geographical association when obtained (e.g., a population density map).

Some of the acquired data may include structured text and/or unstructured text (e.g., from in-hospital data sources, such as clinicians' notes or discharge summaries). Structured data from those unstructured text can be produced by, e.g., extraction through natural language process prior to the geocoding process. In one or more embodiments, data extracted from unstructured text may be tailored to a specific area (such as a population health challenge of interest) by filtering the unstructured text or the extracted data, for example. Structured data may be obtained from public or private sources, such as demographic information from the US Census Bureau or employment data from the US Bureau of Labor and Statistics, and directly geocoded with no further pre-processing required. Geocoding the data may configure the data to create a geospatial database, discussed below.

In one or more embodiments, geocoding may include merging data obtained from disparate sources (structured, unstructured, private, public, demographic, social, socioeconomic, etc.) together with their associated geographical locations as a connector between and among them. Healthcare data geocoded as described may be configured at create a powerful geospatial healthcare database. The criteria for associating particular data with a particular geographical location may be user-defined or predefined and implemented by processing system 120 in accordance with geographic information included with the acquired data. For example, and without limitation, a user may define a region of interest and manually associate specific acquired data with the region of interest (e.g., by "plotting" the data on a map). As another nonlimiting example, census data for a predefined region of interest (e.g., the population density of Baltimore, Md.) may be automatically plotted on a map. Other association options will be apparent to one of ordinary skill and are properly considered within the scope of one or more of the described embodiments. Block 220 may be followed by Block 230. Block 230 (Add Geocoded Data to Database) may refer to processor 123 adding data geocoded in Block 220 to a geospatial database 129. In one or more embodiments, geocoded data may be stored in geospatial database 129 for efficient retrieval analysis in accordance with one or more embodiments discloses herein. Block 230 may be followed by Block 240.

Block 240 (Retrieve and Analyze Geocoded Data) may refer to processor 123 retrieving geocoded data from geospatial database 129 and implementing the OARM for the geocoded data. In one or more embodiments, the OARM may have a plurality of analyzer channels, each of which corresponds to a known risk factor of opioid-associated aberrant behavior. Predictive modeling may allow allocation of channel points based on the statistical sensitivity of specific factors in predicting, for example, opioid-associated mortality. The analyzer channels may be broken down further into analyzer features that provide additional sensitivity in identifying high risk individuals. A base OARM score may be calculated as the summation of points attributed to the analyzer channels.

The following Table shows but one example of a model in which analyzer channels may be assigned to various factors influencing the base score. In one or more embodiments, points may be assigned to each channel. The Table illustrates details of each channel individually in the example, including examples of features that may be used for each channel. It should be noted that not all of the included channels or features need be part of any given analysis. Moreover, other channels and/or features may be suitable in addition or in the alternative, depending on the study or analysis. In one or more embodiments, point modifiers may be applied to one or more of the channels and/or features to affect the influence of the same on the total base score. Nonlimiting examples include percentage weightings, inclusion/exclusion of certain channels/features to suit any particular analysis or subject population, etc.

TABLE

| ANALYZER-CHANNEL | ANALYZER FEATURES |
| --- | --- |
| 01-RESERVED | |
| 02-MEDICAL-ACTIVITY | 02-(MEDICAL-ACTIVITY)(CODE-BLUE) |
| | 02-(MEDICAL-ACTIVITY)(INTUBATION) |
| | 02-(MEDICAL-ACTIVITY)(PRECAUTIONS) |
| 03-CHEMICAL-HEALTH | 03-(CHEMICAL-HEALTH)(DETOX)(REHAB) |
| | 03-(CHEMICAL-HEALTH)(DRUG-ADDICTION) |
| | 03-(CHEMICAL-HEALTH)(NICOTINE-ADDICTION) |
| | 03-(CHEMICAL-HEALTH)(OVERDOSE) |
| | 03-(CHEMICAL-HEALTH)(POT-OPIOID)(ABUSE) |
| | 03-(CHEMICAL-HEALTH)(WITHDRAWAL) |
| 04-DIAGNOSIS | 04-(DIAGNOSIS)(HEPATITIS) |
| | 04-(DIAGNOSIS)(HYPOTENSIVE) |
| | 04-(DIAGNOSIS)(LIVER) |
| | 04-(DIAGNOSIS)(NEUROPATHY) |
| | 04-(DIAGNOSIS)(OVERDOSE) |
| | 04-(DIAGNOSIS)(RENAL) |
| | 04-(DIAGNOSIS)(RESPIRATORY) |
| | 04-(DIAGNOSIS)(SLEEP-DISORDER) |
| 05-PAIN-CONTROL | 05-(PAIN)(CONTROL)(CONSULT-CLINIC) |
| | 05-(PAIN)(CONTROL)(DILAUDID) |
| | 05-(PAIN)(CONTROL)(FENTANYL) |
| | 05-(PAIN)(CONTROL)(KLONOPIN) |
| | 05-(PAIN)(CONTROL)(MANAGEMENT) |
| | 05-(PAIN)(CONTROL)(MS-CONTIN) |
| | 05-(PAIN)(CONTROL)(OTHER) |
| | 05-(PAIN)(CONTROL)(OXYCODONE) |
| | 05-(PAIN)(CONTROL)(OXYCONTIN) |
| | 05-(PAIN)(CONTROL)(PERCOCET) |
| | 05-(PAIN)(CONTROL)(VALIUM) |
| | 05-(PAIN)(CONTROL)(XANAX) |
| 06-PAIN | 06-(PAIN)(PATIENT) |
| | 06-(PAIN)(TYPE)(BACK) |
| | 06-(PAIN)(TYPE)(HEADACHE) |
| | 06-(PAIN)(TYPE)(NEROPATHIC) |
| | 06-(PAIN)(TYPE)(SKELETAL) |

TABLE-continued

| ANALYZER-CHANNEL | ANALYZER FEATURES |
| --- | --- |
| 07-PSYCHOLOGICAL | 07-(PSYCHOLOGICAL)(CONSULT)<br>07-(PSYCHOLOGICAL)(MENTAL-HEALTH)<br>07-(PSYCHOLOGICAL)(SUICIDE-SELF-HARM)<br>07-(PSYCHOLOGICAL)(THERAPY) |
| 08-ABUSE | 08-(ABUSE)(EMOTIONAL)<br>08-(ABUSE)(PHYSICAL)<br>08-(ABUSE)(SEXUAL) |
| 09-LIFESTYLE | 09-(LIFESTYLE)(ALCOHOL)<br>09-(LIFESTYLE)(ANGER-MGMT)<br>09-(LIFESTYLE)(DISABILITY-FINANCIAL)<br>09-(LIFESTYLE)(LEGAL-SYSTEM)<br>09-(LIFESTYLE)(TOBACCO) |
| 10-FAMILY-HISTORY | 10-(FAMILY-HISTORY)(ALCOHOL)<br>10-(FAMILY-HISTORY)(ILLEGAL-DRUGS)<br>10-(FAMILY-HISTORY)(MENTAL-HEALTH)<br>10-(FAMILY-HISTORY)(RX-DRUGS) |
| 11-SOCIAL-WORK | 11-(SOCIAL-WORK)(CONSULT-CONTACT)<br>11-(SOCIAL-WORK)(DEATH)<br>11-(SOCIAL-WORK)(LIFE-CHAOS)<br>11-(SOCIAL-WORK)(PSYCHOSOCIAL)<br>11-(SOCIAL-WORK)(SUPPORT) |
| 12-LAB-TOX | 12-(LABS-TOX)(RESULTS) |
| 13-ILLEGAL-DRUGS | 13-(ILLEGAL-DRUGS)(COCAINE)<br>13-(ILLEGAL-DRUGS)(CRACK)<br>13-(ILLEGAL-DRUGS)(HEROIN)<br>13-(ILLEGAL-DRUGS)(MARIJUANA)<br>13-(ILLEGAL-DRUGS)(METH) |
| 14-MEDICATION (NICOTINE) | 14-(MEDICATION)(NICOTINE)(DOSE-FORM)<br>14-(MEDICATION)(NICOTINE)(ACTION) |
| 15-MEDICATION (DOSE-FORM) | 15-(MEDICATION)(ATIVAN)(DOSE-FORM)<br>15-(MEDICATION)(BUPRENORPHINE)(DOSE-FORM)<br>15-(MEDICATION)(BUTORPHANOL)(DOSE-FORM)<br>15-(MEDICATION)(CODEINE)(DOSE-FORM)<br>15-(MEDICATION)(DARVOCET)(DOSE-FORM)<br>15-(MEDICATION)(DEMEROL)(DOSE-FORM)<br>15-(MEDICATION)(DILAUDID)(DOSE-FORM)<br>15-(MEDICATION)(FENTANYL)(DOSE-FORM)<br>15-(MEDICATION)(HYDROCODONE)(DOSE-FORM)<br>15-(MEDICATION)(KLONOPIN)(DOSE-FORM)<br>15-(MEDICATION)(LORCET)(DOSE-FORM)<br>15-(MEDICATION)(MEPERIDINE)(DOSE-FORM)<br>15-(MEDICATION)(MORPHINE)(DOSE-FORM)<br>15-(MEDICATION)(MS-CONTIN)(DOSE-FORM)<br>15-(MEDICATION)(OXYCODONE)(DOSE-FORM)<br>15-(MEDICATION)(OXYCONTIN)(DOSE-FORM)<br>15-(MEDICATION)(PERCOCET)(DOSE-FORM)<br>15-(MEDICATION)(VALIUM)(DOSE-FORM)<br>15-(MEDICATION)(VICODIN)(DOSE-FORM)<br>15-(MEDICATION)(XANAX)(DOSE-FORM) |
| 16-MEDICATION(ACTION) | 16-(MEDICATION)(ATIVAN)(ACTION)<br>16-(MEDICATION)(BUPRENORPHINE)(ACTION)<br>16-(MEDICATION)(BUTORPHANOL)(ACTION)<br>16-(MEDICATION)(CODEINE)(ACTION)<br>16-(MEDICATION)(DARVOCET)(ACTION)<br>16-(MEDICATION)(DEMEROL)(ACTION)<br>16-(MEDICATION)(DILAUDID)(ACTION)<br>16-(MEDICATION)(FENTANYL)(ACTION)<br>16-(MEDICATION)(HYDROCODONE)(ACTION)<br>16-(MEDICATION)(KLONOPIN)(ACTION)<br>16-(MEDICATION)(LORCET)(ACTION)<br>16-(MEDICATION)(MEPERIDINE)(ACTION)<br>16-(MEDICATION)(MORPHINE)(ACTION)<br>16-(MEDICATION)(MS-CONTIN)(ACTION)<br>16-(MEDICATION)(OXYCODONE)(ACTION)<br>16-(MEDICATION)(OXYCONTIN)(ACTION)<br>16-(MEDICATION)(PERCOCET)(ACTION)<br>16-(MEDICATION)(VALIUM)(ACTION)<br>16-(MEDICATION)(VICODIN)(ACTION)<br>16-(MEDICATION)(XANAX)(ACTION) |
| 17-MEDICATION(DETOX) | 17-(MEDICATION)(ACT-CHARCOAL)(ACTION)<br>17-(MEDICATION)(ACT-CHARCOAL)(DOSE-FORM)<br>17-(MEDICATION)(METHADONE)(ACTION)<br>17-(MEDICATION)(METHADONE)(DOSE-FORM)<br>17-(MEDICATION)(NARCAN)(ACTION)<br>17-(MEDICATION)(NARCAN)(DOSE-FORM)<br>17-(MEDICATION)(SUBOXONE)(ACTION)<br>17-(MEDICATION)(SUBOXONE)(DOSE-FORM) |

The OARM base score may be adjusted based on several variables in order to obtain a risk score used to modify a clinician's behavior, for example. In one or more embodiments, a positive adjustment may be made based on the number of total active channels as well as having channels with greater than five active analyzer features. A negative adjustment may be made for single active channels as well as for having fewer than five active features among all analyzer channels. Additional positive adjustments may be made in accordance with, e.g., NLP, for analyzer features having grammatical phrases of greater than four words. In one or more embodiments, the composite score may be the sum of the base points and adjustment points, although other combinations of these and/or other variables may be employed additionally or as modifications to the above.

For reference and by way of illustration only, with no undue limitation intended, a "channel diversity" risk point boost of 50 points may be given per active channel, it being considered that the more active/diverse model channels, the higher probability/precision. Coincidentally, a 25 point "channel activity" boost may be given for every channel having greater than five markers active, presuming that the more activity in channels, the higher probability/precision. Similarly, a 10 point "4 gram+ marker" boost may be given for every 4-gram or greater marker active, in consideration that longer marker "phrases" (e.g., from a clinician's notes: "pt rec pain meds") may result in higher probability/precision.

On the other hand, a 10% "single channel active point reduction" in total base points may be charged on the presumption that narrower channel activity implies lower probability. Similarly, a "limited active marker point reduction of 10% of total base points may be incurred if fewer than five active markers are present (across all channels), it being considered that fewer markers active equates to lower probability. Block 240 may be followed by Block 250.

Block 250 (Geocode Subjects) may refer to processor 123 geocoding subjects. Once the risk score is determined, the subjects themselves may be geocoded based on, e.g., structured and/or unstructured data such as may be used in the geocoding of data described above. Block 250 may be followed by Block 260.

Block 260 (Map Geocoded Data to Dashboard) may refer to processor 123 mapping the analyzed geocoded data and geocoded subject data to a geohealth dashboard. In one or more embodiments, the geocoded data and geocoded subject data may be output in a format for display or for delivery downstream for further analysis or to direct behavior, policy, or other use. The geocoded data and geocoded subject data may also be fed back to Block 240 in an iterative process such that the output data, in addition to its other benefits, enables machine learning to further enhance and make more effective the risk stratification process. Block 260 may be followed by Block 270 or Block 280.

Block 270 (Display Map) may refer to the outputted geocoded data and geocoded subject data being displayed, e.g., on a display locally by processor 123 or other computing device or remotely by another computing device. In one or more embodiments, the geocoded subject data may be overlaid onto a map developed from social determinants of health data.

Figure 3:
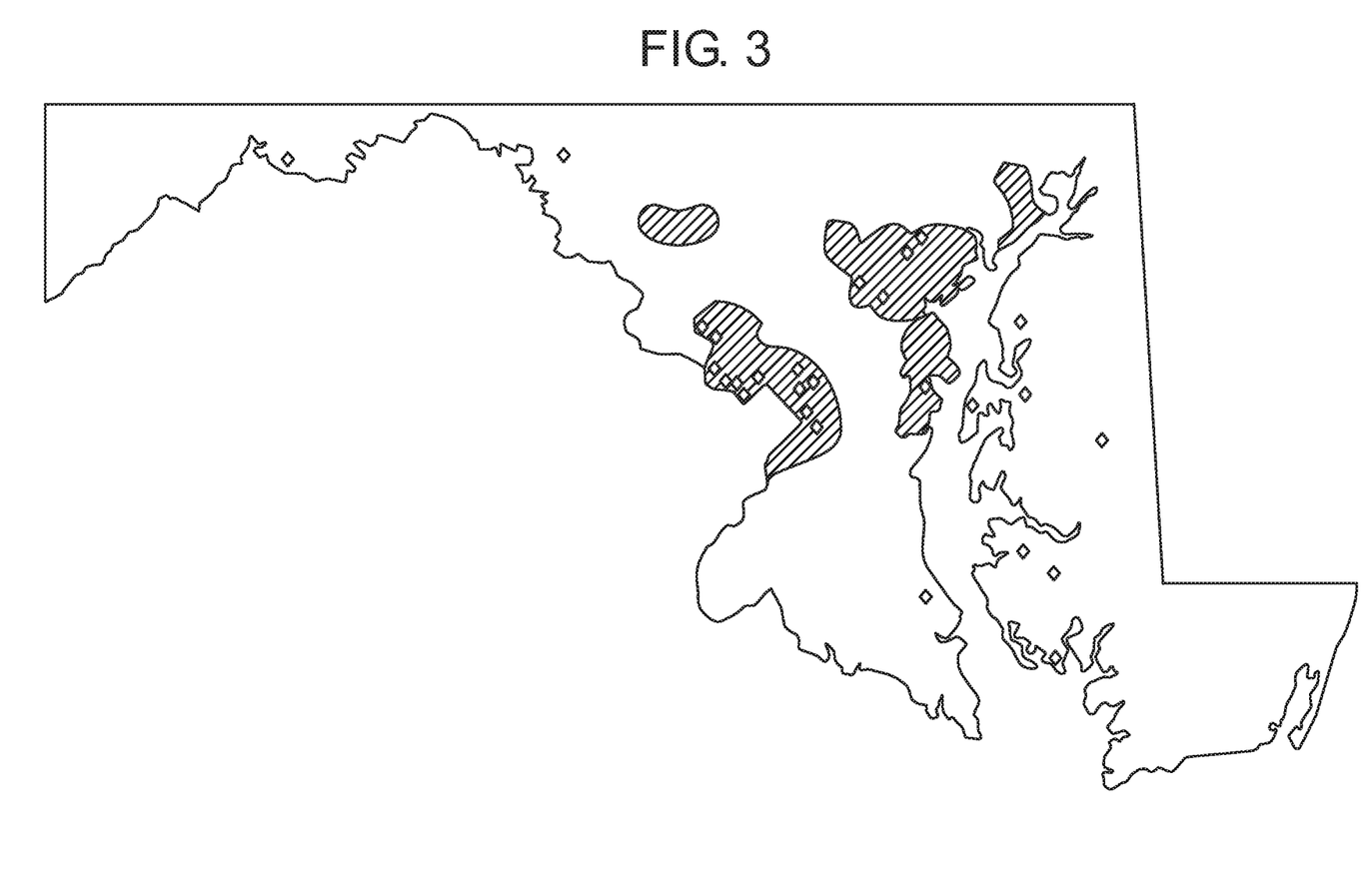
FIG. 3 shows an example map developed from social determinants of health data, illustrating hot zones in accordance with at least some embodiments described herein.

To this and other ends, FIG. 3 shows an example map developed from social determinants of health data, illustrating hot zones in accordance with at least some embodiments described herein. In one or more embodiments, FIG. 3 may indicate, based on the data obtained from data sources 110, regions of opioid-related activity (or activity related to whatever risk is being examined) in Maryland by the shaded areas and locations of treatment facilities by the solid dots, such information being made available by public sources. FIG. 3, of course, illustrates but one example of how mapping from geocoded data can provide a ready visualization of the physical proximity of treatment facilities to areas of greater risk, availability of travel routes from such hot zones to the treatment facilities, political boundaries where local agencies or representatives may be targeted, etc. With knowledge of demographic, economic, and other social determinants, relationships between and among the subject population and social determinants are also readily ascertained by this visual presentation, much more effectively than mere data manipulation or mental analysis, which cannot be effectively performed for the myriad and disparate data, data sources, and correlations that form the foundation for the hot zone map shown in FIG. 3. Block 270 may be followed by Block 280

Block 280 (Deliver Risk Score) may refer to processor 123 or other computing device locally or by a remote computing device delivering a risk score to a downstream user. In one or more embodiments, the risk score provides a risk stratification, e.g., of the likelihood for subjects or subject populations to become addicted, divert opioids from proper channels, or overdose. In turn, the risk stratification may direct the allocation of resources with a geographic- and health-centered focus in response to systemic risks (health, social, economic, safety, etc.) derived from the results of the OARM analysis.

An example (again, for reference and by way of illustration only, with no undue limitation intended) may be made of a logistic regression that demonstrates a sensitivity close to 0.7 with the OARM in the age 45-54 cohort in predicting mortality. The threshold total risk score (base+adjustment) to identify high risk subjects in this example may be set at 4500, with all study patients having at least one ICD-10 (10th Revision of the International Statistical Classification OF Diseases and Related Health Problems) diagnosis related to opioid abuse (recent CDC (Centers for Disease Control) data reveals that opioid overdose is increasing at the greatest rate among individuals in the age 45-54 cohort). Results of such a study may readily suggest many benefits and improvements, including without limitation improved clinician behavior, better contextual response, and smarter allocation of resources to regions populated by the identified high risk subjects.

For example, overdose rates measured in a year prior to implementing the present risk stratification may be compared with rates during implementation as part of a Prescription Drug Monitoring Program (PDMP). Further, clinician behavior (e.g., opioid prescription habits including total opioid prescriptions written, and ordering additional monitoring or behavioral health consultation, etc.) can be compared from the year prior to implementation with the clinician behavior during implementation. This information can be fed back and considered with other empirical information to make and track changes to pain management treatment plans and measure their effectiveness, for example by incorporating this risk stratification into hospital EHR and informatics systems to assist clinicians in treating patients in hospital settings as well as post-discharge.

Figure 4:
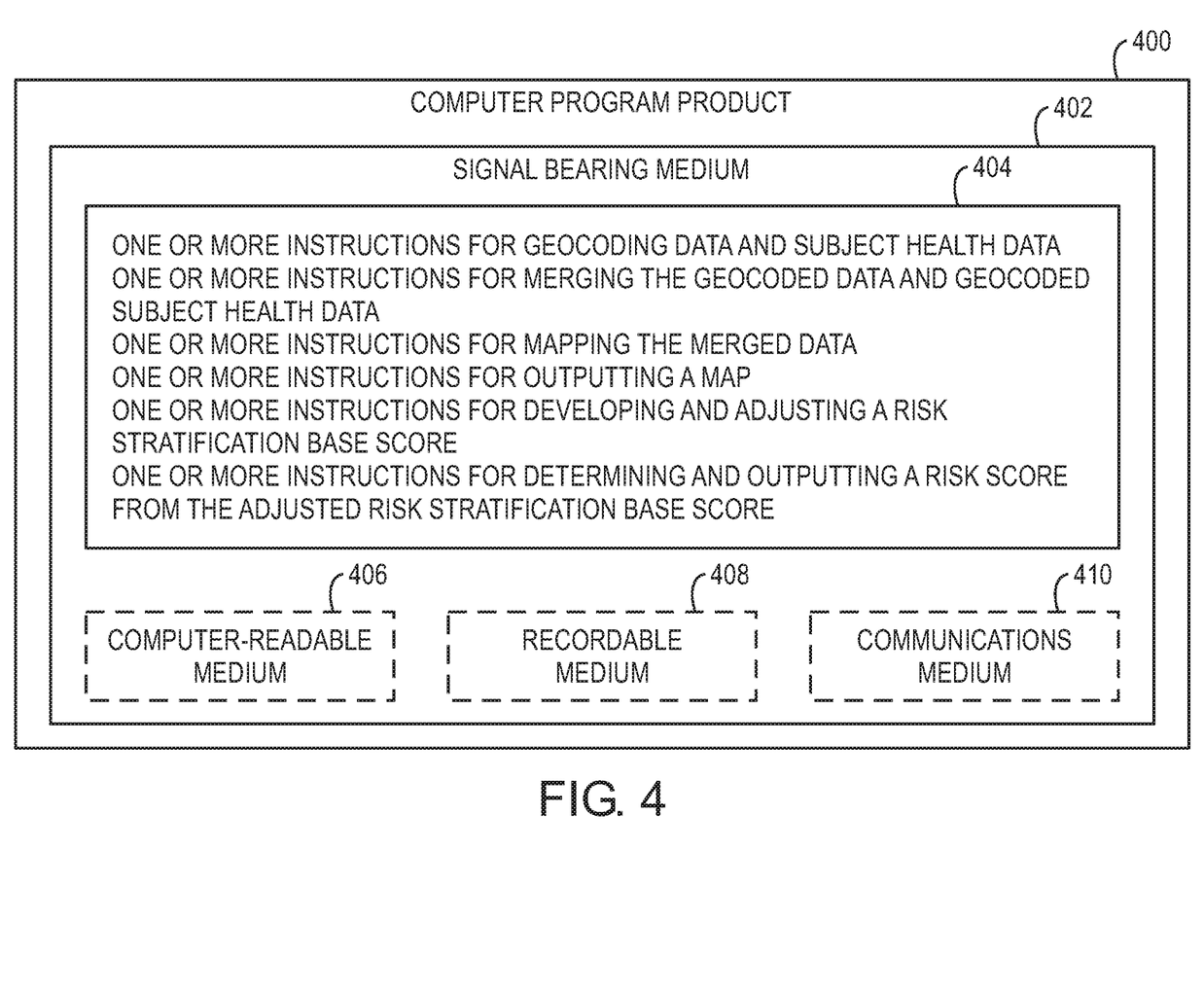
FIG. 4 illustrates computer program products that may be utilized to provide a scheme for risk stratification and response, arranged in accordance with at least some embodiments described herein.

FIG. 4 illustrates computer program products that may be utilized to provide a scheme for risk stratification and response, arranged in accordance with at least some embodiments described herein. Program product 400 may include a signal bearing medium 402. Signal bearing medium 402 may include one or more instructions 404 that, when executed by, for example, a processor, may provide the functionality described above with respect to FIGS. 1A-2. By way of example, but not limitation, instructions 404 may include: one or more instructions for geocoding data; one or more instructions for geocoding health information of a plurality of subjects to produce geocoded subject health data; one or more instructions for merging the geocoded data and geocoded subject health data; one or more instructions for mapping the merged geocoded data and geocoded subject health data to a dashboard; one or more instructions for outputting for display a map visualizing first geographical correlations between at least some of the data and health information derived from the merged geocoded data and geocoded subject health data; one or more instructions for developing a risk stratification base score in accordance with second geographical correlations between at least some of the data and health information derived from the merged geocoded data and geocoded subject health data; one or more instructions for adjusting the risk stratification base score in accordance with positive and/or negative variables; one or more instructions for determining a risk score from the adjusted risk stratification base score; and one or more instructions for outputting the risk score formatted for integration into an electronic health records system. Thus, for example, referring to FIG. 2, processor 123 may undertake one or more of the blocks shown in FIG. 2 in response to instructions 404.

In some implementations, signal bearing medium 402 may encompass a computer-readable medium 406, such as, but not limited to, a hard disk drive, a CD, a DVD, a digital tape, memory, etc. In some implementations, signal bearing medium 402 may encompass a recordable medium 408, such as, but not limited to, memory, read/write (R/W) CDs, R/W DVDs, etc. In some implementations, signal bearing medium 402 may encompass a communications medium 410, such as, but not limited to, a digital and/or an analog communication medium (e.g., a fiber optic cable, a waveguide, a wired communications link, a wireless communication link, etc.). Thus, for example, computer program product 400 may be conveyed to one or more modules of processor 123 by an RF signal bearing medium, where the signal bearing medium is conveyed by a wireless communications medium (e.g., a wireless communications medium conforming with the IEEE 802.11 standard).

Figure 5:
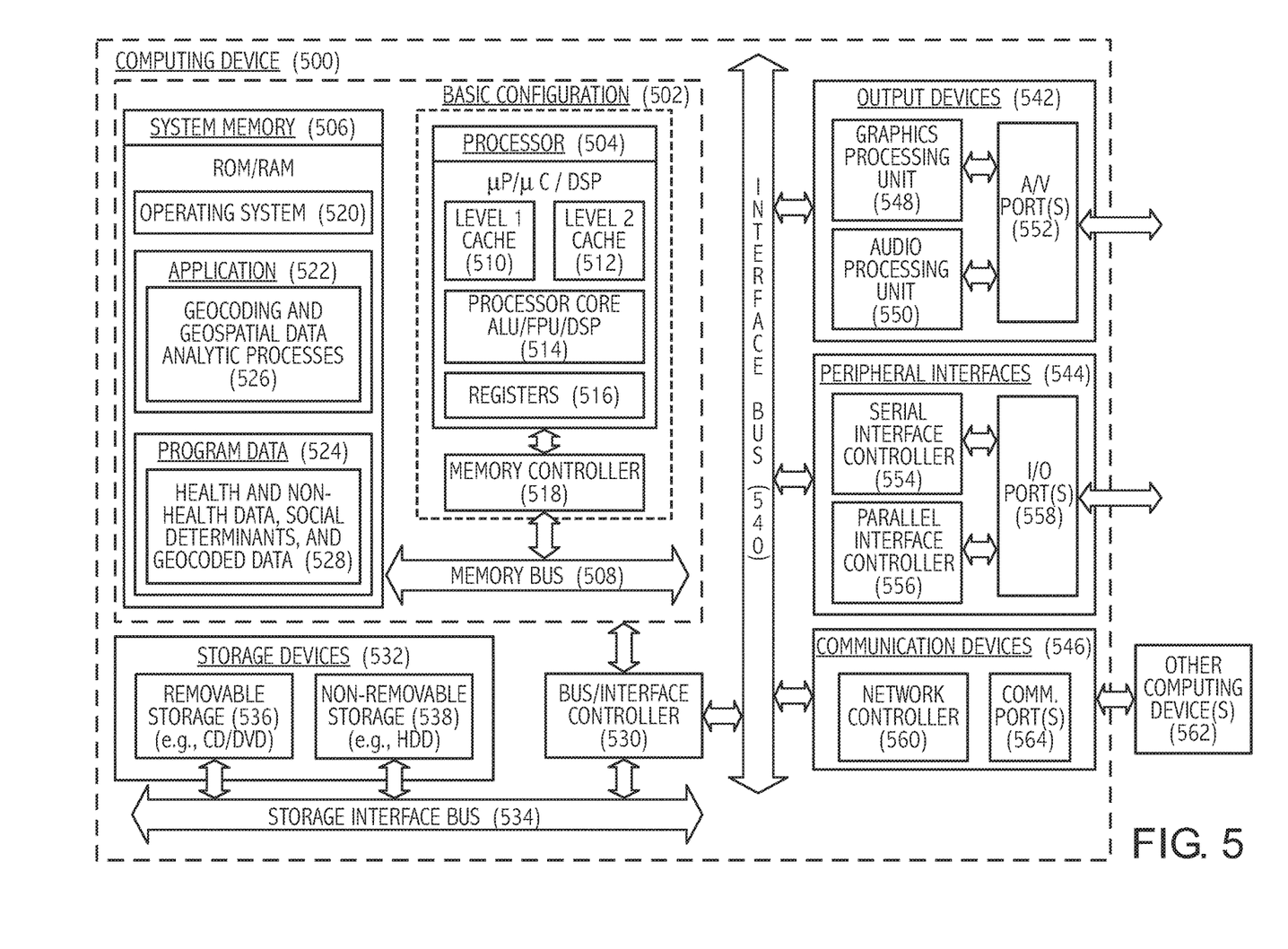
FIG. 5 shows a block diagram illustrating an example computing device by which various example solutions described herein may be implemented, arranged in accordance with at least some embodiments described herein.

FIG. 5 is a block diagram illustrating an example computing device 500 that is arranged for risk stratification in accordance with the present disclosure. In a very basic configuration 502, computing device 500 typically includes one or more processors 504 and a system memory 506. A memory bus 508 may be used for communicating between processor 504 and system memory 506.

Depending on the desired configuration, processor 504 may be of any type including but not limited to a microprocessor (µP), a microcontroller (µC), a digital signal processor (DSP), or any combination thereof. Processor 504 may include one more levels of caching, such as a level one cache 510 and a level two cache 512, a processor core 514, and registers 516. An example processor core 514 may include an arithmetic logic unit (ALU), a floating point unit (FPU), a digital signal processing core (DSP Core), or any combination thereof. An example memory controller 518 may also be used with processor 504, or in some implementations memory controller 518 may be an internal part of processor 504.

Depending on the desired configuration, system memory 506 may be of any type including but not limited to volatile memory (such as RAM), non-volatile memory (such as ROM, flash memory, etc.) or any combination thereof. System memory 506 may include an operating system 520, one or more applications 522, and program data 524. Application 522 may include geocoding, geospatial data analytic, and risk stratification processes 526 that are arranged to perform functions as described herein including those described with respect to process 200 of FIG. 2. Program data 524 may include health and non-health data, social determinants, and geocoded data 528 that may be useful for developing a risk stratification as is described herein. In some embodiments, application 522 may be arranged to operate with program data 524 on operating system 520 such that implementations of risk stratification in, e.g., healthcare systems to assist clinicians in treating patients in clinical settings and post-examination or discharge, as well as to target treatments and non-healthcare responses to risk, may be provided as described herein. This described basic configuration 502 is illustrated in FIG. 5 by those components within the inner dashed line.

Computing device 500 may have additional features or functionality, and additional interfaces to facilitate communications between basic configuration 502 and any required devices and interfaces. For example, a bus/interface controller 530 may be used to facilitate communications between basic configuration 502 and one or more data storage devices 532 via a storage interface bus 534. Data storage devices 532 may be removable storage devices 536, non-removable storage devices 538, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer readable instructions, data structures, program modules, or other data.

System memory 506, removable storage devices 536 and non-removable storage devices 538 are examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 500. Any such computer storage media may be part of computing device 500.

Computing device 500 may also include an interface bus 540 for facilitating communication from various interface devices (e.g., output devices 542, peripheral interfaces 544, and communication devices 546) to basic configuration 502 via bus/interface controller 530. Example output devices 542 include a graphics processing unit 548 and an audio processing unit 550, which may be configured to communicate to various external devices such as a display or speakers via one or more A/V ports 552. Example peripheral interfaces 544 include a serial interface controller 554 or a parallel interface controller 556, which may be configured to communicate with external devices such as input devices (e.g., keyboard, mouse, pen, voice input device, touch input device, etc.) or other peripheral devices (e.g., printer, scanner, etc.) via one or more I/O ports 558. An example communication device 546 includes a network controller 560, which may be arranged to facilitate communications with one or more other computing devices 562 over a network communication link via one or more communication ports 564.

The network communication link may be one example of a communication media. Communication media may typically be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer readable media as used herein may include both storage media and communication media.

Computing device 500 may be implemented as a portion of a small-form factor portable (or mobile) electronic device such as a cell phone, a personal data assistant (PDA), a personal media player device, a wireless web-watch device, a personal headset device, an application specific device, or a hybrid device that include any of the above functions. Computing device 500 may also be implemented as a personal computer including both laptop computer and non-laptop computer configurations.

Embodiments of a system, method, and computer-readable medium for risk stratification and response have been disclosed. In one or more such embodiments, health and non-health information may be geocoded and merged with geocoded subject health data to create a geocoded health database that can be mapped and analyzed to address a range of population health challenges, including individualized and comprehensive responses to the opioid epidemic.

In one or more embodiments, by merging historical EHR data, demographic, geographic, and/or social determinants of health data, risks to individuals from a given population can be stratified to identify those at relatively higher risk of addiction, diversion, and overdose, for example. The algorithm that is defined by this risk stratification can be integrated into hospital EHR and informatics systems to assist clinicians in treating patients in hospital settings as well as post-discharge. Indeed, integration and subject scoring can be automatically performed, the choice depending upon implementation at the particular institution. The direct impact of the OARM is a new way to treat pain and a new way to identify those subjects who need help avoiding or dealing with their addiction.

In this description a number of possible data sources are mentioned. Such sources should not be considered limiting. Other examples of information from disparate data sources may include:

Climate Information
Geographic:
   topography
   urban/rural
   forests/deserts
demographic Information:
   Population, by State, Legislative District, County, Zip Code, Census Block
   Number of Household, per regions as above
   Age, by ranges
   Education, by levels, e.g., Associates, Bachelors, Masters, PhD., etc.
   Employment Transportation Information, including but not limited to:
   Roads
   Public transit systems
Economic data, including, but not limited to:
   Unemployment Rate
   Employment Data
   Income, by ranges
Health system & Hospital data, including but not limited to:
   Readmission data
   Service lines
   Capacity levels
   Clinician notes
   Discharge summaries
   Drug prescriptions written/filled
   Facility location
   Claims data
   Global budget data
ER utilization:
   Readmission rates
   Patient characteristics
Health Data Sets, including but not limited to:
   MIMIC data sets
   c-TAKES data sets
Law Enforcement data, including but not limited to:
   Overdose locations (as reported by police, fire, EMS)
   Drug-related crime rates
Social Media Data, including but not limited to:
   Yelp! reviews
   Twitter feeds
Socioeconomic:
   Transportation
   Income
   Crime rates
   Head start programs
   Support organizations The foregoing description is presented to enable one of ordinary skill in the art to make and use the disclosed embodiments and modifications thereof, and is provided in the context of a patent application and its requirements. Various modifications to the disclosed embodiments and the principles and features described herein will be readily apparent to those of ordinary skill in the art. Thus, the present disclosure is not intended to limit the invention to the embodiments shown; rather, the invention is to be accorded the widest scope consistent with the principles and features described herein.

What is claimed is:

1. A method comprising:
geocoding structured information acquired from a plurality of sources and structured information converted from unstructured information to produce geocoded data;
generating a first database to store the geocoded data;
geocoding health information of a plurality of subjects to produce geocoded subject health data;
merging the geocoded data and geocoded subject health data;
generating a second database to store the merged geocoded data and geocoded subject health data;
displaying a map visualizing geographical correlations between at least some of the health information and the acquired structured information and unstructured information derived from the merged geocoded data and geocoded subject health data;
developing, for each of a plurality of geographical locations in the map, a risk stratification score that conveys a relative likelihood of one or more subject populations in said each geographical location becoming addicted to or overdosing on an opioid, and wherein developing the risk stratification score includes:

establishing a plurality of analyzer channels, wherein each analyzer channel of the plurality of analyzer channels corresponds to a different risk factor category associated with a risk of addiction to or abuse of the opioid, wherein each analyzer channel of the plurality of analyzer channels includes a plurality of analyzer features, and wherein each analyzer feature of the plurality of analyzer features describes a specific risk factor within the risk factor category of the corresponding analyzer channel;

identifying one or more the analyzer features in the health information and the acquired structured information and unstructured information derived from the merged geocoded data and geocoded subject health data;

allocating channel points for each of the plurality of analyzer channels based on a number of analyzer features of said each analyzer channel identified in the health information and the acquired structured information and unstructured information derived from the merged geocoded data and geocoded subject health data;

applying modifiers to the allocated channel points;

summing the allocated channel points of the plurality of analyzer channels to obtain a risk stratification base score;

making positive and/or negative adjustments to the risk stratification base score to obtain the risk stratification score;

wherein the positive adjustments coincide with a) an increasing number of analyzer channels having at least one analyzer feature identified in the health information and the acquired structured information and unstructured information derived from the merged geocoded data and geocoded subject health data and/or b) an increasing number of analyzer features identified in the health information and the acquired structured information and unstructured information derived from the merged geocoded data and geocoded subject health data in a particular analyzer channel; and wherein the negative adjustments coincide with a) a decreasing number of analyzer channels having at least one analyzer feature identified in the health information and the acquired structured information and unstructured information derived from the merged geocoded data and geocoded subject health data and/or b) a decreasing number of analyzer features identified in the health information and the acquired structured information and unstructured information derived from the merged geocoded data and geocoded subject health data in a particular analyzer channel;

outputting the risk stratification scores associated with the plurality of geographical locations and formatted for integration into an electronic health records system of one or more clinicians;

adjusting opioid treatment plans of the one or more clinicians for the one or more subject populations in each of the plurality of geographical locations having risk stratification scores exceeding a predetermined threshold score; and allocating resources to combat opioid abuse and/or addiction to each of the plurality of geographical regions having the risk stratification scores exceeding the predetermined threshold score.

2. The method of claim 1, further comprising:

identifying geographical correlations between the plurality of subjects having a risk of addiction to or abuse of the opioid in common and a facilitator of a component of the risk of addiction to or abuse of the opioid;

incorporating the identified geographical correlations in the risk stratification scores; and mapping the risk stratification scores to an action taken on behalf of the plurality of subjects.

3. The method of claim 2, wherein the risk of addiction to or abuse of the opioid is one of drug addiction, diversion of prescribed drugs, and drug overdose;

wherein the component of the risk of addiction to or abuse of the opioid is a drug; and wherein the facilitator of the component of the risk of addiction to or abuse of the opioid is a source of the drug.

4. The method of claim 3, wherein the drug is an opioid, and the risk stratification scores are for Opioid Abuse Related Mortality.

5. The method of claim 4, wherein the opioid is a legally prescribed drug, and the facilitator is a supplier or prescriber of the opioid.

6. The method of claim 4, wherein the opioid is illegal to prescribe.

7. The method of claim 1, wherein the unstructured information includes notes from the clinician.

8. A system comprising:

a memory to store structured information and unstructured information; and a processor configured to:

geocode the stored structured information and structured information converted from unstructured information to produce geocoded data;

generate a first database to store the geocoded data in the memory;

geocode health information of a plurality of subjects to produce geocoded subject health data;

merge the geocoded data and geocoded subject health data;

generate a second database to store the merged geocoded data and geocoded subject health data;

display a map visualizing first geographical correlations between at least some of the health information and the structured and unstructured information derived from the merged geocoded data and geocoded subject health data;

develop, for each of a plurality of geographical locations in the map, a risk stratification score that conveys a relative likelihood of one or more subject populations in said each geographical location becoming addicted to or overdosing on an opioid, and wherein developing the risk stratification score includes the processor being configured to:

establish a plurality of analyzer channels, wherein each analyzer channel of the plurality of analyzer channels corresponds to a different risk factor category associated with a risk of addiction to or abuse of the opioid, wherein each analyzer channel of the plurality of analyzer channels includes a plurality of analyzer features, and wherein each analyzer feature of the plurality of analyzer features describes a specific risk factor within the risk factor category of the corresponding analyzer channel;

identify one or more the analyzer features in the health information and the acquired structured information and unstructured information derived from the merged geocoded data and geocoded subject health data;

allocate channel points for each of the plurality of analyzer channels based on a number of analyzer features of said each analyzer channel identified in the health information and the acquired structured information and unstructured information derived from the merged geocoded data and geocoded subject health data, apply modifiers to the allocated channel points;

sum the allocated channel points of the plurality of analyzer channels to obtain a risk stratification base score make positive and/or negative adjustments to the risk stratification base score to obtain the risk stratification score;
  wherein the positive adjustments coincide with a) an increasing number of analyzer channels having at least one analyzer feature identified in the health information and the acquired structured information and unstructured information derived from the merged geocoded data and geocoded subject health data and/or b) an increasing number of analyzer features identified in the health information and the acquired structured information and unstructured information derived from the merged geocoded data and geocoded subject health data in a particular analyzer channel, and
  wherein the negative adjustments coincide with a) a decreasing number of analyzer channels having at least one analyzer feature identified in the health information and the acquired structured information and unstructured information derived from the merged geocoded data and geocoded subject health data and/or b) a decreasing number of analyzer features identified in the health information and the acquired structured information and unstructured information derived from the merged geocoded data and geocoded subject health data in a particular analyzer channel;

output the risk stratification scores associated with the plurality of geographical locations and formatted for integration into an electronic health records system of one or more clinicians;

adjust the opioid treatment plans of the one or more clinicians for the one or more subject populations in each of the plurality of geographical locations having risk stratification scores exceeding a predetermined threshold score; and allocate resources to combat opioid abuse and/or addiction to each of the plurality of geographical regions having the risk stratification scores exceeding the predetermined threshold score.

9. The system of claim 8, wherein the processor is further configured to:

identify geographical correlations between the plurality of subjects having a risk of addiction to or abuse of the opioid in common and a facilitator of a component of the risk of addiction to or abuse of the opioid;

incorporate the identified geographical correlations in the risk stratification scores; and map the risk stratification scores to an action taken on behalf of the plurality of subjects.

10. The system of claim 9,
wherein the risk of addiction to or abuse of the opioid is one of drug addiction, diversion of prescribed drugs, and drug overdose;
wherein the component of the risk of addiction to or abuse of the opioid is a drug; and
wherein the facilitator of the component of the risk of addiction to or abuse of the opioid is a source of the drug.

11. The system of claim 10, wherein the drug is an opioid, and the risk stratification scores are for Opioid Abuse Related Mortality.

12. The system of claim 11, wherein the opioid is a legally prescribed drug, and the facilitator is a supplier or prescriber of the opioid.

13. The system of claim 11, wherein the opioid is illegal to prescribe.

14. The system of claim 8,
wherein the unstructured information includes notes from the clinician.

15. A non-transitory computer-readable medium having computer-readable instructions that, if executed by a computing device, cause the computing device to perform operations comprising:

geocoding structured information acquired from a plurality of sources and structured information converted from unstructured information to produce geocoded data;

generating a first database to store the geocoded data;

geocoding health information of a plurality of subjects to produce geocoded subject health data;

merging the geocoded data and geocoded subject health data;

generating a second database to store the merged geocoded data and geocoded subject health data;

displaying a map visualizing geographical correlations between at least some of the health information and the acquired structured information and unstructured information derived from the merged geocoded data and geocoded subject health data;

developing, for each of a plurality of geographical locations in the map, a risk stratification score that conveys a relative likelihood of one or more subject populations in said each geographical location becoming addicted to or overdosing on an opioid, and wherein developing the risk stratification score includes:

establishing a plurality of analyzer channels, wherein each analyzer channel of the plurality of analyzer channels corresponds to a different risk factor category associated with a risk of addiction to or abuse of the opioid, wherein each analyzer channel of the plurality of analyzer channels includes a plurality of analyzer features, and wherein each analyzer feature of the plurality of analyzer features describes a specific risk factor within the risk factor category of the corresponding analyzer channel;

identifying one or more the analyzer features in the health information and the acquired structured information and unstructured information derived from the merged geocoded data and geocoded subject health data;

allocating channel points for each of the plurality of analyzer channels based on a number of analyzer features of said each analyzer channel identified in the health information and the acquired structured information and unstructured information derived from the merged geocoded data and geocoded subject health data;

applying modifiers to the allocated channel points;

summing the allocated channel points of the plurality of analyzer channels to obtain a risk stratification base score;

making positive and/or negative adjustments to the risk stratification base score to obtain the risk stratification score;

wherein the positive adjustments coincide with a) an increasing number of analyzer channels having at least one analyzer feature identified in the health information and the acquired structured information and unstructured information derived from the merged geocoded data and geocoded subject health data and/or b) an increasing number of analyzer features identified in the health information and the acquired structured information and unstructured information derived from the merged geocoded data and geocoded subject health data in a particular analyzer channel; and wherein the negative adjustments coincide with a) a decreasing number of analyzer channels having at least one analyzer feature identified in the health information and the acquired structured information and unstructured information derived from the merged geocoded data and geocoded subject health data and/or b) a decreasing number of analyzer features identified in the health information and the acquired structured information and unstructured information derived from the merged geocoded data and geocoded subject health data in a particular analyzer channel;

outputting the risk stratification scores associated with the plurality of geographical locations and formatted for integration into an electronic health records system of one or more clinicians;

adjusting opioid treatment plans of the one or more clinicians for the one or more subject populations in each of the plurality of geographical locations having risk stratification scores exceeding a predetermined threshold score; and allocating resources to combat opioid abuse and/or addiction to each of the plurality of geographical regions having the risk stratification scores exceeding the predetermined threshold score.

16. The non-transitory computer-readable medium of claim 15, wherein the operations further comprise:

identifying geographical correlations between the plurality of subjects having a risk of addiction to or abuse of the opioid in common and a facilitator of a component of the risk of addiction to or abuse of the opioid;

incorporating the identified geographical correlations in the risk stratification scores; and mapping the risk stratification scores to an action taken on behalf of the plurality of subjects.

17. The non-transitory computer-readable medium of claim 16, wherein the risk of addiction to or abuse of the opioid is one of drug addiction, diversion of prescribed drugs, and drug overdose;

wherein the component of the risk of addiction to or abuse of the opioid is a drug; and wherein the facilitator of the component of the risk of addiction to or abuse of the opioid is a source of the drug.

18. The non-transitory computer-readable medium of claim 17, wherein the drug is an opioid, and the risk stratification scores are for Opioid Abuse Related Mortality.

19. The non-transitory computer-readable medium of claim 18, wherein the opioid is a legally prescribed drug, and the facilitator is a supplier or prescriber of the opioid.

* * * * *